United States Patent [19]

Cereda et al.

[11] Patent Number: 5,468,758
[45] Date of Patent: Nov. 21, 1995

[54] CRYSTALLINE FORMS OF ENDO-2,3-DIHYDRO-N-(8-METHYL)-8-AZABICYCLO[3.2.1]OCT-3-YL)-2-OXO-1H-BENZIMIDAZOLE-1-CARBOXAMIDES

[75] Inventors: Enzo Cereda, Tortona A1; Antoine Ezhaya, Milan; Marco Turconi, Voghere; Enrica Dubini; Grazia Maffione, both of Milan, all of Italy

[73] Assignee: Boehringer Ingelheim Italia S.p.A., Florence, Italy

[21] Appl. No.: 264,104

[22] Filed: Jun. 22, 1994

Related U.S. Application Data

[63] Continuation of Ser. No. 25,448, Mar. 2, 1993, abandoned.

[30] Foreign Application Priority Data

Mar. 26, 1992 [IT] Italy .................................. MI9200720
Mar. 26, 1992 [IT] Italy .................................. MI9200723

[51] Int. Cl.$^6$ ........................ A61K 31/46; C07D 451/12
[52] U.S. Cl. ............................................. 514/304; 548/126
[58] Field of Search ........................... 546/126; 514/304

[56] References Cited

U.S. PATENT DOCUMENTS 5,223,511  6/1993  Turconi et al. ........................ 514/304

OTHER PUBLICATIONS

Sagrada, A; Turconi, M.; Bonali, P.; Schiantarelli, P., Micheletti, R.; Montagna, E; Nicolam M.; Algate, D. R.; Rimoldi, E. M.; and Donetti, A. Cancer Chemother. Pharmacol. (1991) 28:470–474.

Primary Examiner—Johann Richter
Assistant Examiner—Laura L. Stockton
Attorney, Agent, or Firm—Robert P. Raymond; Alan R. Stempel; Mary-Ellen Devlin

[57] ABSTRACT

Crystalline and pharmacologically active monohydrates of endo-2,3-dihydro-N-(8-methyl-8-azabicyclo[3.2.1]oct-3-yl)-2-oxo-1H-benzimidazole-1-carboxamide hydrochloride and of endo-3-ethyl-2,3-dihydro-N-(8-methyl-8-azabicyclo[3.2.1]oct-3-yl)-2-oxo-1H-benzimidazole-1-carboxamide hydrochloride.

2 Claims, 4 Drawing Sheets

INFRARED SPECTROSCOPY (IR) SPECTRA OF COMPOUND 2a (PROFILE A)
AND COMPOUND 1a (PROFILE B)

FIG. 1

DIFFERENTIAL SCANNING CALORIMETRY (DSC) THERMOGRAMS OF COMPOUND 1b (PROFILE A) AND COMPOUND 2b (PROFILE B)

FIG. 2   INFRARED SPECTROSCOPY (IR) SPECTRA OF COMPOUND 2a (PROFILE A) AND COMPOUND 1a (PROFILE B)

FIG. 3 INFRARED SPECTROSCOPY (IR) SPECTRA OF COMPOUND 1b (PROFILE A) AND COMPOUND 2b (PROFILE B)

CRYSTALLINE FORMS OF ENDO-2,3-DIHYDRO-N-(8-METHYL)-8-AZABICYCLO[3.2.1]OCT-3-YL)-2-OXO-1H-BENZIMIDAZOLE-1-CARBOXAMIDES

This is a continuation of application Ser. No. 025,448, filed Mar. 2, 1993, now abandoned.

The present invention relates to the crystalline and pharmacologically active monohydrates of endo-2,3-dihydro-N-(8-methyl-8-azabicyclo[3.2.1]oct-3-yl)-2-oxo- 1H-benzimidazole-1-carboxamide hydrochloride and endo- 3-ethyl-2,3-dihydro-N-(8-methyl-8-azabicyclo[3.2.1]oct- 3-yl)-2-oxo-1H-benzimidazole-1-carboxamide hydrochloride, to the processes for their preparation and to the pharmaceutical compositions containing them. EP 309423 described a group of esters and amides of benzimidazoline-2-oxo-1-carboxylic acid, their physiologically acceptable salts and solvates possessing 5-HT antagonistic properties. These compounds were claimed to be useful in the treatment of chemotherapy and radiation induced nausea and emesis, delayed gastric emptying, gastrointestinal motility disorders, particularly dyspepsia, flatulence, oesophageal reflux, irritable bowel syndrome and hypokinesia. The same compounds were also claimed to be useful in the treatment of certain CNS disorders such as for example motion sickness, migraine, cluster headache, anxiety and psychosis. The anhydrous hydrochloride salts of endo-2,3-dihydro-N-(8-methyl-8-azabicyclo [3.2.1]oct-3-yl)- 2-oxo-1H-benzimidazole-1-carboxamide (compound 1a), endo-3-ethyl-2,3-dihydro-N-(8-methyl-8-azabicyclo-[ 3.2.1]oct-3-yl)-2-oxo-1H-benzimidazole-1-carboxamide hydrochloride (compound 1b) are currently being developed in the clinic as antiemetic and antianxiety agents.

(Compound 1a: R=H)
(Compound 1b: R=$C_2H_5$)

The same compounds show potential as antipsychotic drugs free of extra-pyramidal side effects. The use of compounds 1a and 1b in the treatment of patients suffering from organic mental diseases such as dementia and amnesic syndromes was claimed in the Italian Patent Application no. MI 91 A 001845. Pharmaceutical compositions containing compounds 1a and 1b, as active ingredient, were also claimed in the above mentioned patent applications.

Among different possibilities, the administration of compounds 1a and 1b to patients may be conveniently carried out either by the oral route, employing suitable pharmaceutical preparations such as for example tablets, coated tablets and capsules, or by the rectal route, employing for example suppositories. These administration routes show advantages in comparison with, for example, the parenteral route, because the presence of a doctor or of somebody skilled to give an injection, is not required.

Good manufacturing of the above said preparations useful for the oral administration of a drug substance relies on different parameters which are related to the nature of the drug substance itself. Non-limiting examples of such parameters are the drug stability as starting material in different ambient conditions, the stability during the manufacturing process and the stability in the final pharmaceutical compositions. The drug substance used for the preparation of the above said pharmaceutical compositions should be as pure as possible and its stability upon prolonged storage at different ambient conditions must be checked in order to avoid using a degraded drug or a drug with an unpredictably lower titer than that required for the manufacturing process. In such a case a drug content present in individual tablets or capsules, should be unpredictably lower than that expected. Moisture absorption lowers the titer of the drug substance because of the weight gain due to the water intake. Drugs which tend to absorb moisture must be protected from moisture during prolonged storage for example by adding suitable desiccants or by storing the drug in a room protected from moisture. Furthermore the absorption of moisture may also lower the drug titer during the manufacturing process when the drug is exposed at normal conditions without any moisture protection.

A correct weight distribution of drug in individual capsules or tablets is a critical factor, particularly when a low dosage of drug is required. In order to afford the correct weight distribution, one may reduce the particle size of the drug substance to a suitable value, for example by milling. In fact, particles of little size are better distributed, in homogeneous amount, in the single tablet or capsule. Since milling may be accompanied by a certain degree of degradation of compounds 1a and 1b due to the rather hard conditions required in the process, a high stability to milling represents a considerable advantage since it allows the preparation of capsules and tablets containing the proper amount of drug avoiding the presence of degradation products. Furthermore, during the milling of a product the supply of energy and the stress can produce polymorphic modifications, amortization, variation of the crystal lattice of the form of the solid surface. These alterations play an important role in the different next technological processes and in the biopharmaceutical characteristics.

The stability of a drug substance in pharmaceutical compositions is important in determining the validity period of the pharmaceutical speciality; this period is that in which the drug can be administered without any risks either due to the presence of an excessive amount of potentially dangerous degradation products or due to an unacceptably low content of the active principle with respect to the stated amount. The high stability of a drug substance in the above pharmaceutical preparations at different conditions of storage represents therefore an additional advantage both to the patients and to the manufacturer since storage in controlled conditions is avoided as well as the frequent replacement of expired speciality.

For the above said reasons, any modification of the solid state of a drug substance for oral administration in the form of capsules, tablets or coated tablets which can improve its physical and chemical stability is expected to afford a consistent advantage over less stable forms of the same drug. Non-limiting examples of such modifications include different crystalline forms of the parent drug, also in terms of different or new solvates, and salts with different physiologically acceptable acids or bases, if the drug is amenable to salts formation.

The object of the present invention is therefore the preparation of new crystalline forms of compounds 1a and 1b, which do not show the above mentioned disadvantages.

We have now found novel crystalline monohydrate forms of compounds 1a and 1b (compounds 2a and 2b) which are not specifically claimed in EP 309423 and which possess definite advantages in comparison with the anhydrous forms. In fact compounds 2a and 2b do not absorb moisture both during the storage prior to the manufacturing process of capsules, tablets and coated tablets at different conditions of temperature and relative humidity, and during the process itself; furthermore they are more stable than the respective compounds 1a and 1b during all phases of the above mentioned manufacturing process, particularly during the milling and besides they are more stable to storage in the form of capsules, tablets or coated tablets, at different conditions of temperature and of relative humidity. Moreover, the novel crystalline forms are endowed with antagonist activity at 5-HT receptors. Accordingly, the present invention provides compounds of formula (Compound 2a: R=H)
(Compound 2b: R=C$_2$H$_5$)

together with a process for their preparation and pharmaceutical preparation containing them.

Compounds 2a and 2b may be prepared by dissolving the compounds 1a and 1b, as free base, in a hot aqueous solvent, preferably a hot aqueous alkanol, by adding the required amount of gaseous hydrogen chloride, filtering the resulting solution and letting it cool to room temperature. In a preferred embodiment of the process according to the invention, compound 2a is prepared by using, as an hot aqueous alkanol, hot 85% aqueous ethanol. The crystals of compound 2a may be collected by vacuum filtration and are washed with a small amount of aqueous ethanol. In a preferred embodiment of the process according to the invention, compound 2b is prepared by using, as an hot aqueous alkanol, hot 95% aqueous isopropanol. The crystals of compound 2b may be collected by vacuum filtration and are washed with a small amount of aqueous isopropanol. The so obtained crystals of 2a and 2b can be desiccated at a temperature between room temperature and 60° C. under vacuum, most preferably at 40° C. under 0.1 mm Hg vacuum for 24 hours without any appreciable loss of water content. Water content may be measured by usual techniques such as the Karl Fischer test. Alternatively, compounds 2a and 2b may be conveniently prepared by dissolving the anhydrous form of compounds 1a and 1b, as hydrochloride, in hot aqueous ethanol, preferably 85% ethanol (respectively in hot aqueous isopropanol, preferably 95% isopropanol) and allowing to cool the solution at room temperature; crystals of compound 2a (respectively 2b), separated from the cooled solution, are collected by vacuum filtration and manipulated as previously described. In a further option compounds 2a and 2b may be also prepared by dissolving the corresponding compounds 1a and 1b, as a free base in an anhydrous hot alcoholic solvent, preferably anhydrous ethanol (respectively anhydrous isopropanol), and adding to the filtered solution 37% aqueous hydrochloric acid. The crystals of compound 2a (or 2b) separated from the cooled solution are collected by vacuum filtration and manipulated as above described.

In another option the same compounds may be prepared by exposing compounds 1a or 1b to a humidified atmosphere of, for example, air or nitrogen at a temperature between room temperature and 40° C., preferably at room temperature. Water absorption may require variable time according mainly to the size of the crystals of the starting compounds and to the relative humidity. The process is over when no further increase in weight is recorded. The water content may be conveniently measured by Karl Fischer assay and for 2a is usually between 5.07%+0.5; for 2b between 4.70 ±0.5, which contents are indicative of a monohydrate. Compounds 1a and 1b, used in the form of free base as starting material for the preparation of compounds 2a and 2b, may be conveniently prepared as described in the example 16 respectively 14, of EP 309423.

Compounds 2a and 2b are novel crystalline monohydrate forms of compounds 1a and 1b. They show different physico-chemical properties and exist in well defined chemical and crystalline structures. In compounds 2a and 2b, the molecules of water are tightly bound into the crystal lattice and the ratio between the drug molecules and the water molecules is 1.

The analytical characterization of compounds 2a and 2b can be performed by different methods, such as Elemental Analysis, Differential Scanning Calorimetry (DSC), Thermal Gravimetric Analysis (TGA), Infrared Spectroscopy (IR), X-Rays Powder Diffraction, Single Crystal X-Ray Diffraction.

Differential Scanning Calorimetry (DSC)

Differential Scanning Calorimetry. (DSC) was performed by using a Mettler TA 3000 System equipped with TC 10A Processor and DSC 20 cell. The compound (3.5 mg) was weighted in a standard Alumina crucible. It was sealed with crimped-on lid on which three little holes were made.

Compound 2a

The sample was heated in nitrogen flow of 40 ml/min, starting from 30° C. to a final temperature of 320° C. at a rate of 10° C./min. Compound 2a showed an endothermic peak due to crystallization water desorption at 110°–160° C., followed by an exothermic peak due to crystal rearrangement.

Finally the compound melts at 295° C.

Compound 2b

Heating crystals of compound 2b in nitrogen flow of 40 ml/min, starting from 30° C. to a final temperature of 270°

Figure 1:
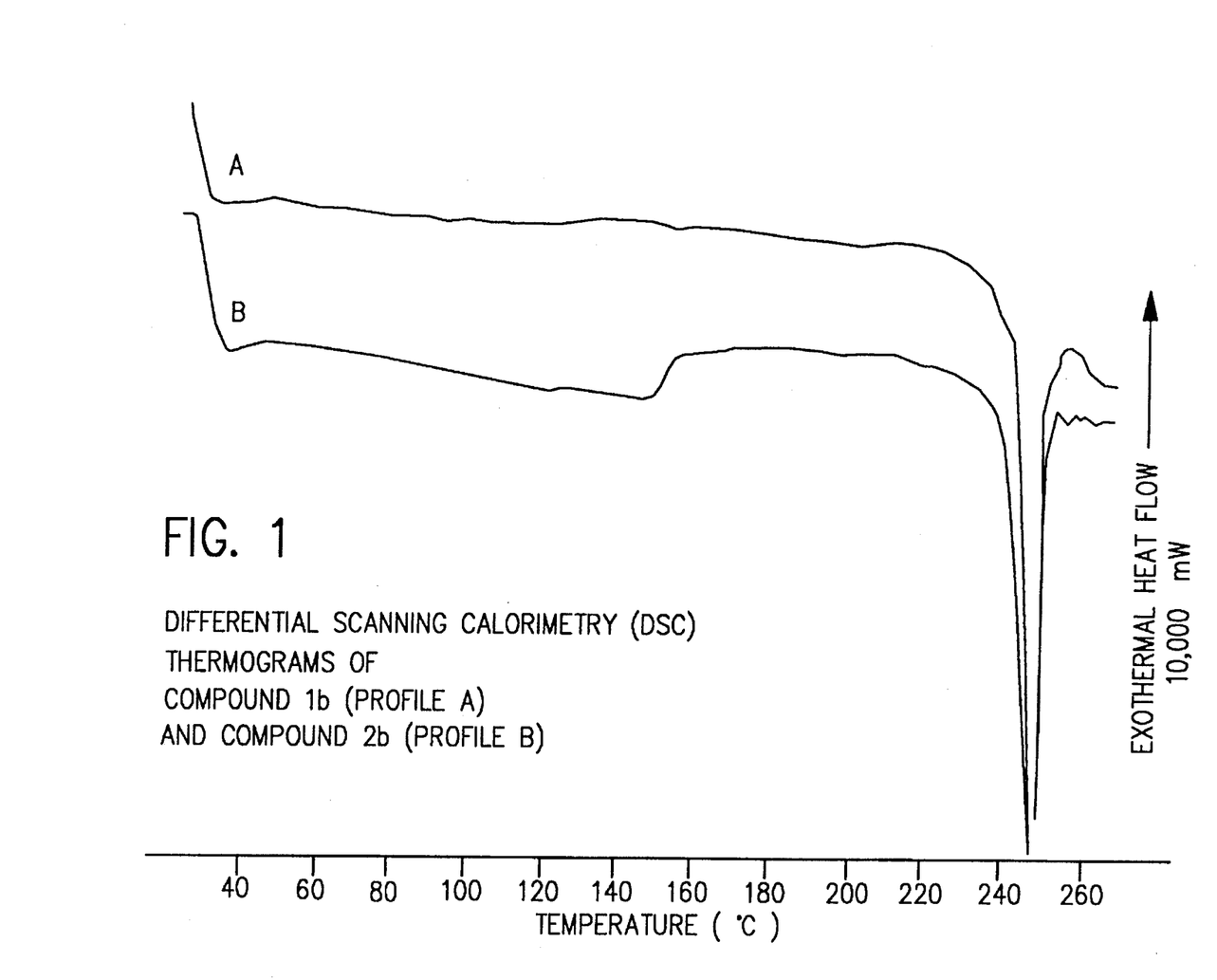
FIG. 1 is Differential Scanning Calorimetry (DSC) Thermograms Compound 1b (Profile A) and Compound 2b (Profile B) depicting the desorption of water of crystallization.

C. at a rate of 10° C./min, leads to the desorption of the water of crystallization in the range between 70° C. and 160° C., as shown by the presence of an endothermic event with a temperature value of 150° C. at the peak maximum (see FIG. 1, Profile B), absent in the thermogram of the anhydrous form (see FIG. 1, Profile A). In FIG. 1 the X-axis reports the temperature range in Centigrade (°C.), the Y-axis the heat flow measured in milli walt (m W). Finally the compound melts at 245° C.

Thermal Gravimetric Analysis (TGA)

Thermal Gravimetric Analysis (TGA) was performed by using a Mettler TA 3000 System equipped with TC 10-A Processor, TG 50 oven and M3 balance. 10 mg of the compound under investigation were weighted in a standard Alumina Crucible.

Compound 2a

Heating was done in a nitrogen flow 200 ml/min., starting from 25° C. to a final temperature of 295° C., at a rate of 10° C./min. Compound 2a showed a weight loss in correspondence of the peak due to crystallization water desorption equal to 5.2%, a value very close to the theoretical value of 5.07% requested for the monohydrate.

Compound 2b

Heating was done in a nitrogen flow, 200 ml/min., starting from 25° C. to a final temperature of 255° C., at a rate of 10° C./min. Compound 2b showed a weight loss in correspondence of the peak due to crystallization water desorption equal to 4.62%, a value very close to the theoretical value of 4.70% requested for the monohydrate.

Infrared Spectroscopy

Infrared spectra of compound 1a, 1b, 2a and 2b were recorded on a Perkin-Elmer Mod 298 infrared spectrophotometer. The compounds were analysed as solid in nujol mull.

Figure 2:
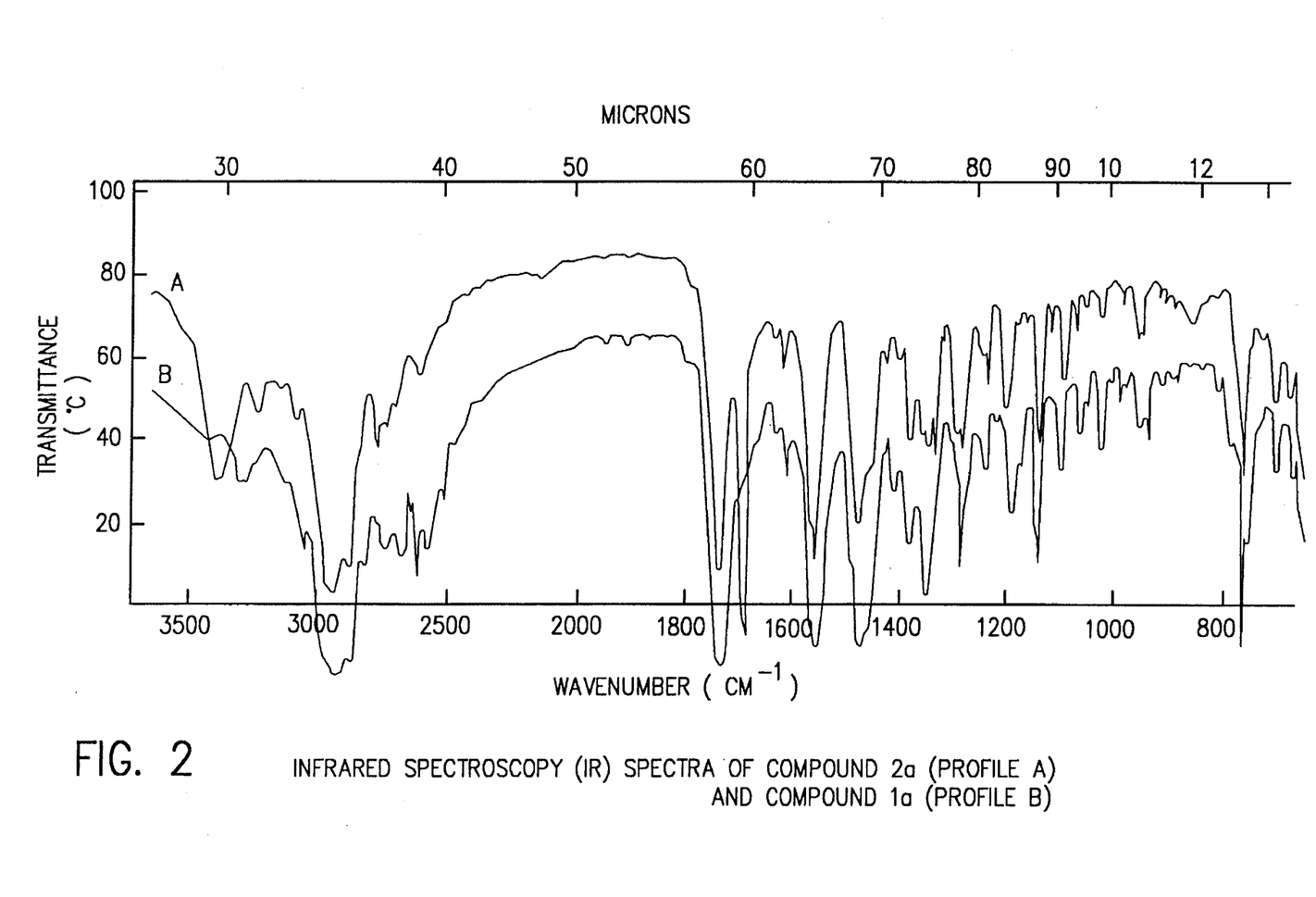
FIG. 2 is Infrared Spectroscopy (IR) Spectra of Compound 2a (Profile A) and Compound 1a (Profile B).

In the infrared spectrum, compound 2a shows a strong band at 3,400 $cm^{-1}$ which is due to the stretching of the hydroxyl groups of water. This band is absent in the corresponding spectrum of compound 1a. Other differences in the peak shape and their relative intensity are evident at 2,600, 1,430–1,390, 1,350, 1,240, 1,170, 1,110, 1,050, 1,000–900 and 850–750 $cm^{-1}$. These show that compounds 1a and 2a are different crystalline forms of the same substance. FIG. 2 shows the IR Spectra of Compound 2a (Profile A) and Compound 1a (Profile B) respectively. The X-axis reports the values of wavenumber ($cm^{-1}$), the Y-axis the percentages of transmittance.

Figure 3:
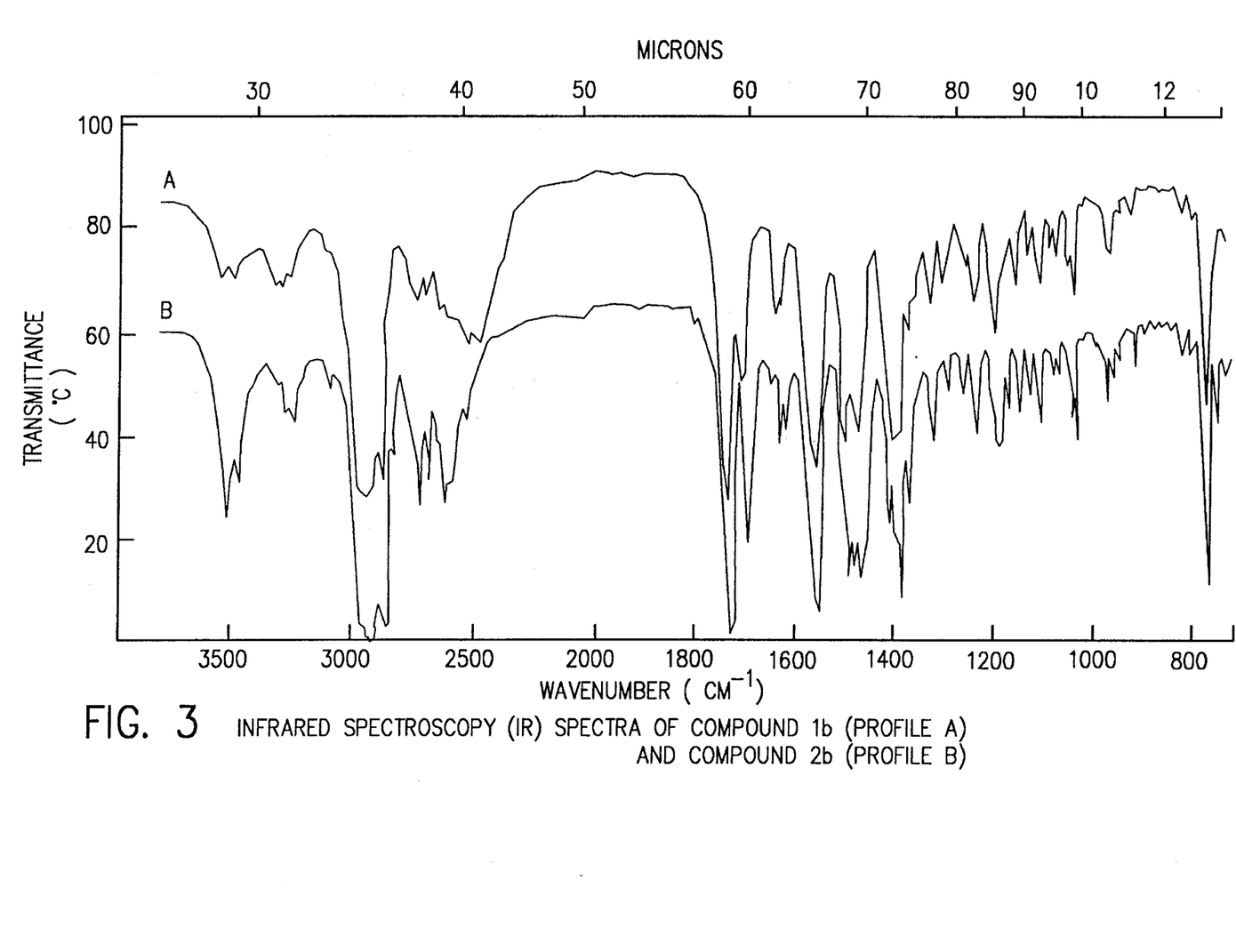
FIG. 3 is Infrared Spectroscopy (IR) Spectra of Compound 1b (Profile A) and Compound 2b (Profile B).

In the infrared spectrum, compound 2b shows a strong band at 3500 $cm^{-1}$ which is due to the stretching of the hydroxyl groups of water. This band is almost negligible in the corresponding spectrum of compound 1b. Other differences in the peak shape and their relative intensity are evident at 2600–2500, 1680, 1630, 1480, 1400–1350, 1300–1200, 1160–1100, 1060, 1030, 950–900 and about 750 $cm^{-1}$. These show that compounds 1b and 2b are different crystalline forms of the same substance. FIG. 3 shows the IR Spectra of Compound 1b (Profile A) and Compound 2b (Profile B) respectively. The X-axis reports the values of wavenumber ($cm^{-1}$), the Y-axis the percentages of transmittance.

X-ray Powder Diffraction Pattern

The analysis was carried out in a Philips PW 1800/10 diffractometer equipped with a Digital Microvax 2000 computer on which a Philips APD 1700 program was installed. Setting up parameters, along with main characteristics of the diffractometer are reported below:

goniometer scan range: 2° ≤ 2 θ precision: 0.001° 2 θ scan speed: 0.02°/second scan type: continuous analysis time: 40 min.

slits.

soller slits automatic divergence slits (ADS)

reciving slit: 0.3 mm detector slit: 0.8 mm

X ray type tube: Cu (long fine focus)

wavelengths (λ): $K_{\alpha 1}$=1.54060A $K_{\alpha 2}$=1.54439A generator hight voltage: 40 kV tube current: 20 mA kV and mA stabilization: 0.0005% per % mains varation general irradiated sample length: 10 mm monochromator: graphite crystal proportional detector time constant: 2

Figure 4:
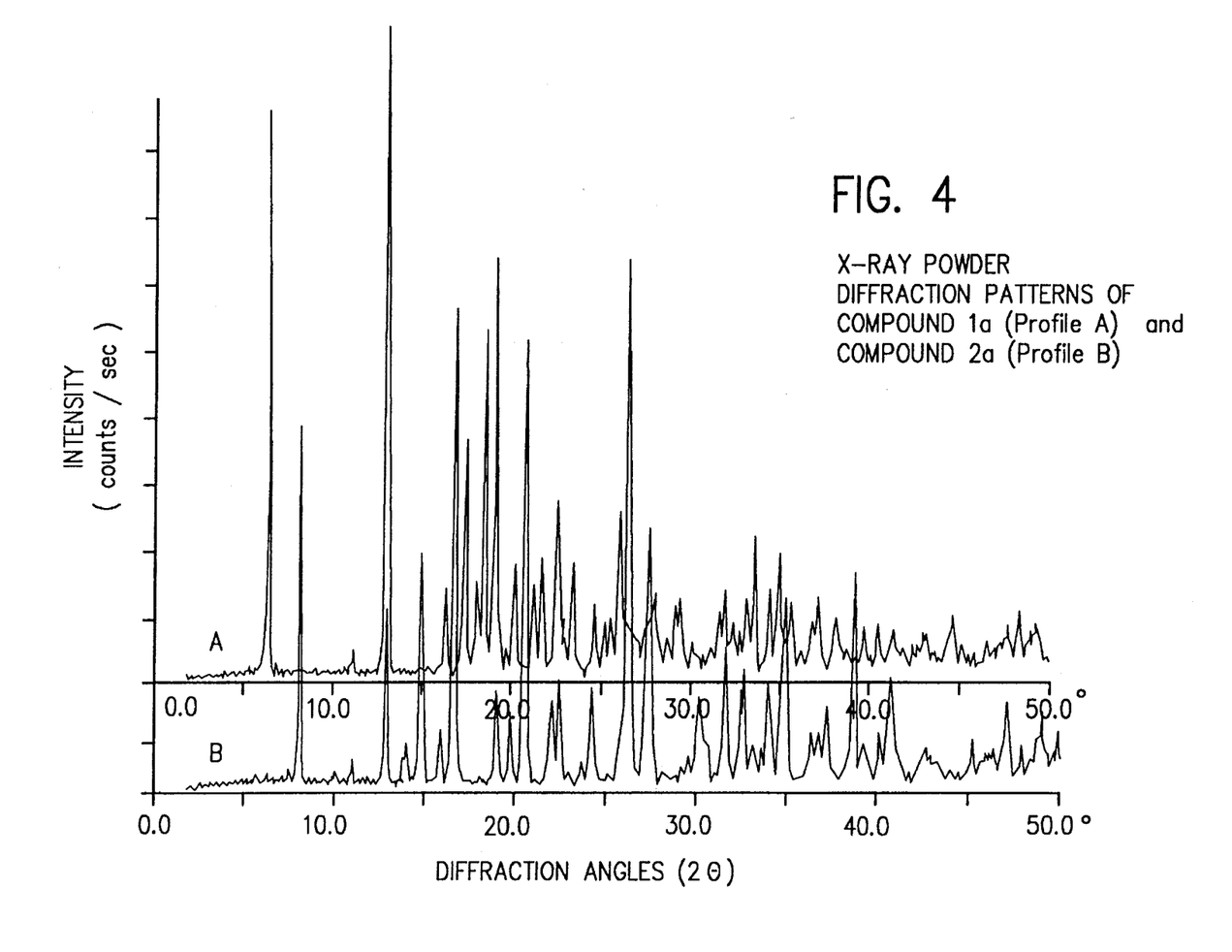
FIG. 4 is X-ray Powder Diffraction Patterns of Compound 1a (Profile A) and Compound 2a (Profile B).

The most significant parameters of the main peaks, namely the angles of diffraction (degrees), the values of the interplanar spacings (D), the absolute (Peak/Counts) and relative ($I/I_{max}$) intensities are shown in Table I and II for compounds 1a and 2a respectively. Significant differences between compound 1a and 2a are particularly evident if we compare the peaks connected with diffraction angles of 6, 13 and 17.6–20 degrees for compound 1a and of 8, 15, 16.8, 21, 26.1 and 26.3 degrees for compound 2a, as shown in FIG. 4, which reports the X-ray Powder Diffraction Patterns of Compound 1a (Profile A) and Compound 2a (Profile B). In FIG. 4, the X-axis shows the values of diffraction angles 2θ, the Y-axis shows the peak intensities measured in counts/sec.

TABLE I

| | COMPOUND 1a | | | |
|---|---|---|---|---|
| Peak no. | Angle (deg) | D spac (Ang) | Peak (cts) | I/I max (%) |
| 1 | 6.6425 | 13.2961 | 2440. | 51.26 |
| 2 | 7.0300 | 12.5641 | 23. | 0.48 |
| 3 | 11.3150 | 7.8138 | 98. | 2.06 |
| 4 | 13.2800 | 6.6617 | 4761. | 100.00 |
| 5 | 15.0550 | 5.8801 | 31. | 0.66 |
| 6 | 16.5550 | 5.3505 | 388. | 8.15 |
| 7 | 16.9550 | 5.2252 | 76. | 1.59 |
| 8 | 17.6150 | 5.0309 | 1037. | 21.78 |
| 9 | 18.3100 | 4.8414 | 376. | 7.91 |
| 10 | 18.7525 | 4.7282 | 1576. | 33.10 |
| 11 | 19.3500 | 4.5835 | 1892. | 39.74 |
| 12 | 19.6425 | 4.5159 | 234. | 4.92 |
| 13 | 19.9525 | 4.4464 | 102. | 2.14 |
| 14 | 20.4825 | 4.3326 | 467. | 9.80 |
| 15 | 21.5450 | 4.1212 | 380. | 7.99 |
| 16 | 21.9850 | 4.0397 | 471. | 9.89 |

TABLE I-continued

COMPOUND 1a

| Peak no. | Angle (deg) | D spac (Ang) | Peak (cts) | I/I max (%) |
|---|---|---|---|---|
| 17 | 22.7725 | 3.9018 | 751. | 15.77 |
| 18 | 23.1850 | 3.8333 | 207. | 4.36 |
| 19 | 23.6150 | 3.7645 | 480. | 10.07 |
| 20 | 24.8125 | 3.5854 | 292. | 6.14 |
| 21 | 25.3800 | 3.5065 | 222. | 4.66 |
| 22 | 25.7275 | 3.4599 | 219. | 4.60 |
| 23 | 26.2050 | 3.3980 | 713. | 14.97 |
| 24 | 26.7125 | 3.3346 | 790. | 16.58 |
| 25 | 26.9050 | 3.3111 | 369. | 7.74 |
| 26 | 27.4925 | 3.2417 | 188. | 3.94 |
| 27 | 27.8325 | 3.2029 | 250. | 5.24 |
| 28 | 28.1550 | 3.1669 | 353. | 7.42 |
| 29 | 28.7925 | 3.0982 | 144. | 3.02 |
| 30 | 29.2775 | 3.0480 | 299. | 6.29 |
| 31 | 29.4950 | 3.0260 | 306. | 6.43 |
| 32 | 30.1225 | 2.9644 | 121. | 2.54 |
| 33 | 31.1900 | 2.8653 | 102. | 2.14 |
| 34 | 31.6225 | 2.8271 | 266. | 5.58 |
| 35 | 31.9350 | 2.8002 | 346. | 7.27 |
| 36 | 32.3500 | 2.7652 | 219. | 4.60 |
| 37 | 33.1125 | 2.7032 | 317. | 6.65 |
| 38 | 33.5750 | 2.6670 | 590. | 12.40 |
| 39 | 34.4900 | 2.5983 | 353. | 7.42 |
| 40 | 35.0025 | 2.5615 | 506. | 10.63 |
| 41 | 35.7225 | 2.5115 | 303. | 6.36 |
| 42 | 36.8525 | 2.4370 | 204. | 4.30 |
| 43 | 37.1650 | 2.4172 | 310. | 6.51 |
| 44 | 38.0900 | 2.3606 | 228. | 4.79 |
| 45 | 39.2350 | 2.2943 | 144. | 3.02 |
| 46 | 39.7675 | 2.2648 | 159. | 3.33 |
| 47 | 40.5000 | 2.2255 | 172. | 3.60 |
| 48 | 41.2575 | 2.1864 | 166. | 3.50 |
| 49 | 42.4050 | 2.1299 | 121. | 2.54 |
| 50 | 43.1425 | 2.0952 | 151. | 3.18 |
| 51 | 44.6975 | 2.0258 | 237. | 4.98 |
| 52 | 45.1750 | 2.0055 | 121. | 2.54 |
| 53 | 46.5625 | 1.9489 | 117. | 2.45 |
| 54 | 47.6750 | 1.9060 | 202. | 4.24 |
| 55 | 48.3575 | 1.8807 | 259. | 5.44 |
| 56 | 49.4600 | 1.8413 | 177. | 3.73 |

TABLE II

COMPOUND 2a

| Peak no. | Angle (deg) | D spac (Ang) | Peak (cts) | I/I max (%) |
|---|---|---|---|---|
| 1 | 7.6775 | 11.5058 | 40. | 1.88 |
| 2 | 8.2700 | 10.6828 | 1505. | 71.46 |
| 3 | 10.2450 | 8.6274 | 36. | 1.71 |
| 4 | 11.1675 | 7.9167 | 76. | 3.59 |
| 5 | 13.0450 | 6.7812 | 751. | 35.63 |
| 6 | 13.9225 | 6.3557 | 106. | 5.04 |
| 7 | 14.1635 | 6.2485 | 164. | 7.78 |
| 8 | 14.9850 | 5.9074 | 1018. | 48.30 |
| 9 | 15.9525 | 5.5512 | 190. | 9.04 |
| 10 | 16.0700 | 5.5109 | 231. | 10.97 |
| 11 | 16.8750 | 5.2498 | 2107. | 100.00 |
| 12 | 19.1650 | 4.6273 | 392. | 18.61 |
| 13 | 19.2575 | 4.6053 | 388. | 18.42 |
| 14 | 19.9475 | 4.4475 | 310. | 14.70 |
| 15 | 20.8125 | 4.2646 | 1998. | 94.84 |
| 16 | 22.0550 | 4.0271 | 306. | 14.54 |
| 17 | 22.2300 | 3.9958 | 335. | 15.90 |
| 18 | 22.5475 | 3.9402 | 454. | 21.53 |
| 19 | 23.0250 | 3.8596 | 35. | 1.65 |
| 20 | 23.7750 | 3.7395 | 67. | 3.19 |
| 21 | 24.3300 | 3.6554 | 400. | 18.99 |
| 22 | 25.7500 | 3.4570 | 207. | 9.84 |
| 23 | 26.1500 | 3.4050 | 1505. | 71.46 |
| 24 | 26.3450 | 3.3802 | 2098. | 99.56 |

TABLE II-continued

COMPOUND 2a

| Peak no. | Angle (deg) | D spac (Ang) | Peak (cts) | I/I max (%) |
|---|---|---|---|---|
| 25 | 27.2225 | 3.2732 | 655. | 31.11 |
| 26 | 27.4725 | 3.2440 | 1089. | 51.69 |
| 27 | 29.5325 | 3.0223 | 74. | 3.51 |
| 28 | 29.9775 | 2.9784 | 234. | 11.11 |
| 29 | 30.1725 | 2.9596 | 324. | 15.38 |
| 30 | 30.5650 | 2.9225 | 190. | 9.04 |
| 31 | 31.4925 | 2.8385 | 650. | 30.86 |
| 32 | 32.3725 | 2.7633 | 380. | 18.05 |
| 33 | 32.5925 | 2.7452 | 462. | 21.94 |
| 34 | 32.9925 | 2.7128 | 128. | 6.06 |
| 35 | 33.5200 | 2.6713 | 146. | 6.95 |
| 36 | 33.9450 | 2.6388 | 412. | 19.56 |
| 37 | 34.8125 | 2.5750 | 784. | 37.21 |
| 38 | 36.3250 | 2.4712 | 182. | 8.65 |
| 39 | 36.7950 | 2.4407 | 210. | 9.98 |
| 40 | 37.1375 | 2.4190 | 306. | 14.54 |
| 41 | 38.5925 | 2.3310 | 900. | 42.72 |
| 42 | 39.0700 | 2.3036 | 161. | 7.66 |
| 43 | 40.1000 | 2.2468 | 193. | 9.17 |
| 44 | 40.6450 | 2.2179 | 458. | 21.74 |
| 45 | 42.5125 | 2.1247 | 121. | 5.74 |
| 46 | 43.2675 | 2.0894 | 90. | 4.28 |
| 47 | 45.2500 | 2.0023 | 177. | 8.40 |
| 48 | 46.3950 | 1.9556 | 114. | 5.43 |
| 49 | 47.1150 | 1.9273 | 324. | 15.38 |
| 50 | 47.9125 | 1.8971 | 146. | 6.95 |
| 51 | 48.9800 | 1.8582 | 299. | 14.21 |
| 52 | 49.9000 | 1.8261 | 210. | 9.98 |

Also the difference of the crystalline form of compounds 1b and 2b is further supported by X-ray powder diffraction pattern.

Single Crystal X-Ray Diffraction

The analysis was carried out on a prismatic crystal of compound 2a of dimension equal to 0.41×0.23×0.08 min. A Philips PW 1100 four-circle diffractometer equipped with a graphite monochromator was used. 48 Reflections (2<θ<25°) were used to measure lattice parameters with a Philips LAT routine. Other important experimental parameters were the following:

ω—2 θ scan mode, scan speed 0.05 $S^{-1}$, scan width 2.0°, range 2°–22°. Three standard reflections every 180 min, mean intensity variation 1.5% max intensity variations 2.6%. 4201 independent data [$-11 \leq 11$; $12 \leq k \leq 12$; $1 \leq 14$], max (sin θ/λ=0.53$A^{-1}$]; 2085 unique reflections, 1186 with I>3(I). The structure was solved by direct method (MULTAN 80, XANADU). Figures were drawn with ORTEP II.

The analysed compound (formula $C_{16}H_{20}N_4O_2.HCl.H_2$, Mw=354,84) possesses a monoclinic P2$_1$/c cell, a= 11.668 A, b=11.714 A, c=13.672 A, α=90°, β= 114.83°, γ=90°. The water molecule in the crystalline structure of compound 2a occupies a well defined space in the crystal lattice being bonded through a hydrogen bond to the unsubstituted nitrogen atom of the benzimidazolone ring. Moreover the same molecule of water is linked to two chloride ions belonging to two other drug molecules.

Compound 2b is characterized by the following data:
Formula $C_{18}H_{24}N_4O_2.HCl.H_2O$, Mw=382.9; needle like crystal from isopropanol with dimensions of 0.1×0.1×0.55 mm; monoclinic, space group P21/C, a=13.869(2), b=16.449(2), c=8.550(1) A, β=97.64(1)°, V= 1933.1(5)$A^3$, Z=4, $d_{calc}$=1.316 g/cm$^3$.

The figures in the ( ) are the standard deviation of the last figure. The density of the crystal was determined with the mixed solvent of carbontetrachloride and benzene, and it was 1.313 g/cm$^3$.

Moisture Sorption/Desorption Studies

The determination of the sorption isotherms was carried out in a hygrostat.

At suitable intervals, the sample was weighed by means of a sample balance. The atmosphere in the hygrostat and therefore around the sample of compound 1a (1b) and 2a (2b) was conditioned and kept by a saturated solutions of a suitable salt:

Li Cl saturated solution 11.3% RH/25° C. 11.2% RH/37° C.
Mg(NO$_3$)$_2$ saturated solution 52.8% RH/25° C. 49.2% RH/37° C.
Na Cl saturated solution 75.3% RH/25° C. 74.8% RH/37° C.
KNO$_3$ saturated solution 93.7% RH/25° C. 90.0% RH/37° C.

At the end of the experiment, after completing the hysteresis, that is the adsorption—desorption cycle of humidity, the compound was assayed for the title and degradation products by TLC and HPLC, the physical state by DSC and water content by TGA.

Compound 2a is stable in condition of storage at different temperatures and relative humidity (RH) as reported in table III in comparison with compound 1a, which the contrary, shows a marked tendency to moisture absorption.

TABLE III

| Duration | Compound 1a Relative humidity | | Compound 2a Relative humidity | |
|---|---|---|---|---|
| | 75% | 94% | 75% | 94% |
| Room Temperature | | | | |
| 2 h | 0.68 | 1.28 | 5.46 | 5.49 |
| 4 h | 0.74 | 1.92 | 5.43 | 5.53 |
| 6 h | 0.78 | 2.41 | 5.37 | 5.51 |
| 1 d | 1.25 | 5.33 | 5.41 | 5.49 |
| 4 d | 2.54 | 5.39 | 5.42 | 5.44 |
| 8 d | 3.50 | 5.39 | 5.36 | 5.48 |
| 20 d | 4.59 | 5.40 | 5.41 | 5.49 |
| 40 d | 4.95 | 5.42 | — | — |
| 37° C. | | | | |
| 2 h | 0.34 | 1.93 | 5.80 | 5.49 |
| 4 h | 0.39 | 3.41 | 5.75 | 5.47 |
| 6 h | 0.59 | 4.68 | 5.79 | 5.53 |
| 1 d | 1.95 | 5.04 | 5.75 | 5.50 |
| 5 d | 5.09 | 5.06 | 5.80 | 5.49 |
| 9 d | 5.13 | 5.06 | 5.76 | 5.48 |
| 15 d | 5.13 | 5.04 | 5.80 | 5.48 |

As a consequence, storage of compound 2a may be effected in normal conditions and no particular precautions are needed to avoid exposure to moisture. The titer of compound 2a, when it is stored in normal conditions, is therefore maintained at difference with compound 1a which, in the same conditions, may show different titles according to the water content. The hygroscopicity may also influence the drug title immediately after the manufacturing of tablets. In fact during the process of manufacturing the drug exposed at normal ambient conditions where it can take up moisture. As emphasized in table IV compound 1a increases its water content in comparison with compound 2a which shows a stable water content during the mixing (a) and tableting (b) phases.

TABLE IV

| | Moisture content(*) | |
|---|---|---|
| | compound 1a | compound 2a |
| Start | 0.62% | 4.90% |
| Intermediate (a) | 0.66% | 4.90% |
| Final (b) | 1.02% | 4.90% |

(*)expressed as % on the weight of compound 1a.

The drug content in individual tablets is therefore more foreseable and reproducible when using compound 2a instead of compound 1a.

As reported in Table V the water content of compound 2a is not affected in the employed conditions, even in conditions of extreme dryness (11 RH, 37° C.). The physical stability is therefore an substantial advantage of compound 2a; its title is stable over a wide range of conditions and its storage and handling are absolutely unproblematic unlike compound 1a.

TABLE V

| At 37° C. | Compound 2a 11.2% RH |
|---|---|
| 0 | 5.26$^{a)}$ |
| 2 h | 5.32 |
| 4 h | 5.31 |
| 6 h | 5.31 |
| 21 days | 5.29 |

$^{a)}$water content expressed as % on the weight of compound 1a.

Compound 2b is stable in condition of storage at different temperatures and relative humidity (RH) as reported in table VI in comparison with compound 1b, which on the contrary, shows a marked tendency to moisture absorption.

TABLE VI

| Duration | Compound 1b Relative humidity | | Compound 2b Relative humidity | |
|---|---|---|---|---|
| 37° C. | 49.2% | 74.8% | 49.2% | 74.8% |
| 0 | 1.13 | 1.13 | 5.00 | 5.00 |
| 2 h | 2.18 | 4.99 | 5.03 | 5.05 |
| 4 h | 2.58 | 4.93 | 5.04 | 5.05 |
| 6 h | 3.01 | 4.97 | 5.00 | 5.07 |
| 1 d | 4.07 | 4.90 | 5.00 | 5.07 |
| 4 d | 4.81 | 4.92 | 5.04 | 5.07 |
| 10 d | 4.82 | 4.85 | 4.95 | 4.97 |
| 30 d | 4.81 | 4.81 | 5.02 | 5.00 |

As a consequence, storage of compound 2b may be effected in normal conditions and no particular precautions are needed to avoid exposure to moisture. The titer of compound 2b, when it is stored in normal conditions, is therefore maintained at difference with compound 1b which, in the same conditions, may show different titer according to the water content.

As reported in Table VII the water content of compound 2b is not affected in the employed conditions, even in conditions of extreme dryness (11 RH, 37° C.). The physical stability is therefore an substantial advantage of compound 2b; its title is stable over a wide range of conditions and its storage and handling are absolutely unproblematic unlike compound 1b.

TABLE VII

| At 37° C. | Compound 2b 11.2% RH |
|---|---|
| 0 | 5.02[a)] |
| 1 h | 5.00 |
| 2 h | 4.85 |
| 4 h | 4.80 |
| 6 h | 4.70 |
| 6 days | 4.70 |

[a)]water content expressed as % on the weight of compound 1b.

Milling Studies and Uniformity Content

The milling process was performed by the FRITSCH Pulverisette 14 Rotor Speed Mill supplied with circular sieve stainless steel with trapezoidal 0.080 mm diameter openings. The samples were passed through the mill twice at 20.000 rpm motor speed. The sample is assayed for title and degradation products by TLC and HPLC, physical state by DSC, water content by TGA, particle size distribution by Mercury Instrusion Porosimetry. The milled compounds are formulated in capsules and tablets at very low dose level (0.5 mg) by direct mixing and direct compression manufacturing method, respectively.

On the finished solid dosage forms, the uniformity content test was carried out by determining the compound content at least for 10 individual capsules or tablets. The coefficient of variation has than be less to 15% in order to accept the formulation.

Compound 2a shows an unexpected better stability to milling in comparison with compound 1a. The percentage of degradation products after milling compounds 1a and 2a at a rotor speed of 20,000 rpm is 0.65% and 0.0% respectively. In the meantime, the particle size reduction which is another relevant parameter indicative of the milling efficiency, reaches the same rank order for the two compounds as shown by Mercury Porosimetry Analysis.

The higher stability of compound 2a to milling constitutes a more significative advantage over compound 1a since higher titers of the active drug can be achieved in the final compositions and the presence of a relevant content of degradation products is avoided.

Compound 2b shows an identical stability to milling in comparison with compound 1b with similar efficacy; in fact the particle size reduction which is another relevant parameter indicative of the milling efficiency, reaches the same rank order for the two compounds as shown by Mercury Porosimetry Analysis.

The higher physical stability of compound 2b to milling (compound 1b passes from a humidity content of 0.87% to 2.32%, whereas compound 2b remains unchanged to 4.8%) constitutes a more significative advantage over compound 1b since higher titers of the active drug can be achieved in the final compositions and the presence of a relevant content of humidity can be avoided.

Compounds 2a and 2b show a better stability in tablets and capsules in comparison with compounds 1a and 1b after prolonged storage at different conditions (as reported for 2a in tables VIII, IX and X). Drug stability in these final compositions may be measured in accelerated stability tests or in long term real time stability tests. In accelerated stability tests, the above pharmaceutical compositions are exposed at high temperatures at different degrees of relative humidity for a period of time. Such tests are considered to be indicative of the stability of the composition at normal conditions. In long term real time stability studies the final compositions are exposed to normal conditions of storage at ambient temperatures at different degrees of relative humidity. In both the accelerated stability tests and in the long term real time stability tests, compounds 2a and 2b show a better stability than that of compound 1a and 1b.

TABLE VIII

| ACCELERATED STABILITY TESTS | | |
|---|---|---|
| | Compound 1a % degradation | Compound 2a % degradation |
| 1 month/55° C.(*) | 2.0% | 0.5% |
| 3 months/55° C. | 3.2% | 1.6% |

(*)according to H. Leven Berger Pharm. Act. Helv. 50 (1975) 88–91 it is equivalent to 2 years storage at room temperature. Tablets and capsules are packaged in PVC/PVDC blister with aluminium foil.

TABLE IX

| ACCELERATED STABILITY TESTS | | |
|---|---|---|
| | Compound 1a % degradation | Compound 2a % degradation |
| 3 months/40° C.-75% RH(*) | 0.8% | 0.5% |
| 6 months/40° C.-75% RH | 1.7% | 1.0% |

(*)according to "Guidelines for stability studies for Human Drugs and Biologics" (1987) (USA/FDA) it is equivalent to 2 years at room temperature. Tablets and capsules are packaged in PVC/PVDC blister with aluminium foil.

TABLE X

| LONG-TERM REAL TIME STABILITY TESTS | | |
|---|---|---|
| | Compound 1a % degradation | Compound 2a % degradation |
| 3 months/40° C. | 0.6% | 0.4% |
| 6 months/30° C.-70% RH | 0.5% | 0.1% |
| 6 months/40° C. | 1.1% | 0.6% |

Tablets and capsules are packaged in PVC/PVDC blister with aluminium foil.

Consequently the packaging of compounds 2a and 2b may be conveniently carried out by using conventional materials without any need to employ films or special materials in order to protect the integrity of a hygroscopic or, however, less stable product.

According to a further feature of the present invention, there are provided pharmaceutical compositions comprising as active ingredient an effective amount of compounds 2a or 2b, as hereinbefore defined, in association with pharmaceutical carriers or excipients. Particularly preferred are the compositions for the systemic administration, in particular for oral administration.

The pharmaceutical compositions according to the present invention are obtained by known methods, for example by conventional methods of mixing, granulation, tableting and film-coating. Thus, for example, it is possible to obtain pharmaceutical compositions for oral administration by mixing compound 2a or 2b with one or more solid carriers, and the obtained mixture is optionally granulated and worked by adding other excipients so that tablets or cores to film-coating can be obtained.

Suitable in particular diluents such carriers are as lactose, mannitol, sorbitol and/or dicalcium phosphate, furthermore humid binders such as corn starch, maize starch, methylcellulose, hydroxypropylmethylcellulose, polyvinylpyrrolidone and/or, if desired, disintegrants such as alginic acid or sodium alginate, starches, cellulose derivatives, polyvinylpyrrolidone.

Further excipients are glidants and lubricants, such as colloidal silicon dioxide acid, talc, stearic acid, magnesium or calcium stearate and/or polyethylenglycol or its derivatives.

The cores to film-coat may be covered with suitable coatings, in case gastro-resistent, using concentrated sugary solutions, which optionally contain gum arabic, talc, polyvinylpyrrol idone, polyethylenglycol and/or titanium dioxide, solutions of lacquer in suitable organic or aqueous solvents for the production of gastro-resistent coating, solutions of suitable cellulose compounds, such as acetylcellulose phthalate or copolymers of acrylic and metacrylic acid. Additional excipients, for example flavoring and colouring agents may also be present.

The pharmaceutical compositions for oral administration may also be presented as hard gelatine capsules. The se capsules may contain compound 2a, respectively 2b, mixed with diluents such as lactose, cellulose, calcium phosphate, glidants and lubricant such as talc or magnesium stearate, and/or disintegrants such as starches, cellulose derivatives, polymers. In the soft capsules compound 2a (or 2b) is mixed with suitable liquid excipients such as arachis oil, paraffin oil, polyethylenglycol or propylenic glycol, solutions of starch hydrogenated derivatives.

The pharmaceutical compositions for rectal administration are in the form of suppositories containing compound 2a (2b) with conventional suppository bases, such as cocoa butter or other glycerides.

The compositions are advantageously formulated at dosage units, each dosage unit being adapted to supply a single dose of the achive ingredient. Each dosage unit may conveniently contain from 0.1 to 20 mg and preferably from 0.2 to 15 mg of the above ingredient The following examples illustrate the present invention without limiting its scope

EXAMPLE 1

Endo-2,3-dihydro-N-(8-methyl-8-azabicyclo[3.2.1]-oct-3-yl)- 2-oxo-1H-benzimidazole-1-carboxamide, hydrochloride monohydrate (compound 2a)

Endo-2,3-dihydro-N-(8-methyl-8-azabicyclo[3.2.1]oct-3-yl)- 2-oxo-1H-benzimidazole-1-carboxamide (48 g, 0.178 mol) was dissolved into 85% aqueous ethanol (400 ml) under heating and stirring. Gaseous hydrochloric acid was then bubbled into the filtered clear solution until an acid pH is obtained. After two days standing at room temperature the separated white crystals were collected by filtration, washed with 85% aqueous ethanol (50 ml) and dried under vacuum at 40° C. for 24 hours. 43.5 g of the title compound were obtained $H_2O$ (K.F.) Found % 5.04 Calc. % 5.08 Analysis Found % C 54.10 H 6.50 N 15.74 Cl 9.95 $C_{16}H_{20}N_4O_2.H_2O.HCl$ Calc. % C 54.16 H 6.53 N 15.79 Cl 9.99

EXAMPLE 2

Compound 2a

Endo-2,3-dihydro-N-(8-methyl-8-azabicyclo[3.2.1]oct-3-yl)- 2-oxo-1H-benzimidazole-1-carboxamide, hydrochloride (100 g, 0.3 mol) was dissolved into a solution of 95% ethanol (740 ml) and water (87 ml) by gentle heating. After filtering, the clear solution was left at room temperature for two days. The separated crystals were collected by filtration, washed with 85% ethanol (50 ml) and dried under vacuum at the temperature of 40° C. for two days. 65.5 g of the title compound were obtained $H_2O$ (K.F.) Found % 4.99 Calc. % 5.08 Analysis Found % C 54.21 H 6.48 N 15.83 Cl 9.95 $C_{16}H_{20}N_4O_2.H_2O.HCl$ Calc. % C 54.16 H 6.53 N 15.79 Cl 9.99

EXAMPLE 3

Compound 2a

Endo-2,3-dihydro-N-(8-methyl-8-azabicyclo[3.2.1]oct-3yl)- 2-oxo-1H-benzimidazole-1-carboxamide (5 g, 0.0166 mol) was dissolved in anhydrous ethanol (40 ml) by gentle heating. Then a solution of 37% hydrochloric acid (3 ml) and water (4 ml) was slowly added to the filtered hot solution. The crystals, which separated from the solution left for two days at room temperature, were filtered, washed with aqueous 85% ethanol (5 ml) and dried under vacuum for 24 hours at the temperature of 40° C. 3.6 g of the title compound were obtained $H_2O$ (K.F.) Found % 5.00 Calc. % 5.08 Analysis Found % C 54.20 H 6.50 N 15.70 Cl 10.02 $C_{16}H_{20}N_4O_2.H_2O.HCl$ Calc. % C 54.16 H 6.53 N 15.79 Cl 9.99

EXAMPLE 4

Endo-3-ethyl-2,3-dihydro-N-(8-methyl-8-azabicyclo-[ 3.2.1]oct-3-yl)-2-oxo-1H-benzimidazole-1-carboxamide, hydrochloride monohydrate (compound 2b)

Endo-3-ethyl-2,3-dihydro-N-(8-methyl-8-azabicyclo-[3.2.1]oct-3-yl)-2-oxo-1H-benzimidazole-1-carboxamide as base (10 g, 30.4 mol) was dissolved into an aqueous solution of 95% isopropanol (80 ml) under heating and stirring. Gaseous hydrochloric acid was bubbled into the filtered solution until an acid pH is obtained. For resting from the solution the desired compound as hydrochloride monohydrate was separated by crystallizing. This was filtered, washed with humidified isopropanol and dried under vacuum at 40° C. for 24 hours, 10.5 g, M.p. 244°–245° C., KF 4.68%

Analysis Found % C 56.10 H 7.04 N 14.51 $C_{18}H_{24}N_4O_2.HCl.H_2O$ Calc. % C 56.46 H 7.11 N 14.63

EXAMPLE 5

Compound 2b

Endo-3-ethyl-2,3-dihydro-N-(8-methyl-8-azabicyclo-[ 3.2.1]oct-3-yl)-2-oxo-1H-benzimidazole-1-carboxamide, hydrochloride was dissolved into a solution of isopropanol (15 ml) and water (0.5 ml) under heating. The hot solution was filtered and allowed to cool spontaneously. The desired compound was separated, filtered, washed with humidified isopropanol and dried under vacuum for 24 hours at 40° C., 2.85 g, M.p. 241°– 243° C., KF 4.75%

Analysis Found % C 56.20 H 7.13 N 14.56 $C_{18}H_{24}N_4O_2.HCl.H_2O$ Calc. % C 54.46 H 7.11 N 14.63

EXAMPLE 6

Compound 2b

Endo-3-ethyl-2,3-dihydro-N-(8-methyl-8-azabicyclo-[3.2.1]oct-3-yl)-2-oxo-1H-benzimidazole-1-carboxamide (240 g, 0.73 moli) was dissolved into isopropanol (2360 ml) under stirring and heating. The solution was filtered and an aqueous solution of 37% hydrochloric acid (125 ml). For resting, the desired product was spontaneously separated, filtered, washed with 95% aqueous isopropanol and dried under vacuum at 40° C. for 24 hours. 260 g were obtained, 243°–245° C., KF 4.7%

Analysis Found % C 55.97 H 7.00 N 14.54 $C_{18}H_{24}N_4O_2.HCl.H_2O$ Calc. % C 56.41 H 7.11 N 14.63

EXAMPLE 7

| Tablets | |
|---|---|
| compound 2a (or 2b) | 0.5 mg |
| lactose | 140.8 mg |
| corn starch | 36.0 mg |
| silica colloidal | 1.8 mg |
| magnesium stearate | 0.9 mg |

Method of preparation: compound 2a (or 2b), lactose and corn starch were mixed and homogeneously wetted with water. After screening of the moist mass and drying in a tray drier, the mixture was again passed through a screen and silica colloidal and magnesium stearate were added. Then the mixture was pressed into tablets weighing 180 mg each. Each tablet contains 0.5 mg of compound 2a (2b).

EXAMPLE 8

| Capsules | |
|---|---|
| compound 2a | 0.5 mg |
| lactose | 227.1 mg |
| corn starch | 58.0 mg |
| silica colloidal | 2.9 mg |
| magnesium stearate | 1.5 mg |

Method of preparation: compound 2a was mixed with auxiliary products, and the mixture was passed through a screen and mixed homogeneously in a suitable device. The resulting mixture was filled into hard gelatine capsules (290 mg per capsule); each capsule contains 0.5 mg of compound 2a.

EXAMPLE 9

| Capsules | |
|---|---|
| compound 2b | 5.0 mg |
| lactose | 210.5 mg |
| corn starch | 60.0 mg |
| silica colloidal | 3.0 mg |
| magnesium stearate | 1.5 mg |

Method of preparation: compound 2b was mixed with auxiliary products, and the mixture was passed through a screen and mixed homogeneously in a suitable device. The resulting mixture was filled into hard gelatine capsules (280 mg per capsule); each capsule contains 5 mg of compound 2b.

EXAMPLE 10

| Suppositories | |
|---|---|
| compound 2a (2b) | 15 mg |
| semisynthetic glicerides of fatty acids | 1185 mg |

Method of preparation: The semisynthetic glicerides of fatty acids were melted and the compound 2a (2b) was added while stirring homogeneously. After cooling at a proper temperature the mass was poured into preformed moulds for suppositories weghing 1200 mg each. Each suppository contains 15 mg of compound 2a (2b).

We claim:

1. Crystalline monohydrates of endo-2,3-dihydro-N-(8-methyl- 8-azabicyclo[3.2.1.]oct-3-yl)-2-oxo-1H-benzimidazole- 1-carboxamide hydrochloride and endo-3-ethyl- 2,3-dihydro-N-(8-methyl-8-azabicyclo[3.2.1]oct-3-yl)-2-oxo-1H-benzimidazole-1-carboxamide hydrochloride, of formula (Compound 2a: R=H)
(Compound 2b: R=$C_2H_5$).

2. A pharmaceutical composition comprising, as active ingredient, a therapeutically active amount of crystalline monohydrate of endo-2,3-dihydro-N-(8-methyl- 8-azabicyclo[3.2.1]oct-3-yl)-2-oxo-1H-benzimidazole- 1-carboxamide hydrochloride, or endo-3-ethyl-2,3-dihydro-N-(8-methyl-8-azabicyclo-[ 3.2.1]oct-3-yl)-2-oxo-1H-benzimidazole-1-carboxamide hydrochloride, according to claim 1 in association with pharmaceutical carriers or excipients.

* * * * *